(12) United States Patent
Gurbuz et al.

(10) Patent No.: US 12,002,374 B2
(45) Date of Patent: Jun. 4, 2024

(54) METHOD AND SYSTEM FOR AUTOMATED GUIDANCE TO A SUBJECT TO BUILD HEALTHY CHEWING HABITS TO FACILITATE ADHERENCE TO A HEALTHY FOOD INTAKE ROUTINE

(71) Applicants: Julia Hatice Gurbuz, Campbell, CA (US); Alara Ipek Gurbuz, Campbell, CA (US); Altay Gurbuz, Campbell, CA (US)

(72) Inventors: Julia Hatice Gurbuz, Campbell, CA (US); Alara Ipek Gurbuz, Campbell, CA (US); Altay Gurbuz, Campbell, CA (US)

( * ) Notice: Subject to any disclaimer, the term of this patent is extended or adjusted under 35 U.S.C. 154(b) by 0 days.

(21) Appl. No.: 18/107,481

(22) Filed: Feb. 8, 2023

(65) Prior Publication Data

US 2023/0377479 A1    Nov. 23, 2023

Related U.S. Application Data

(63) Continuation-in-part of application No. PCT/TR2022/050424, filed on May 17, 2022.

(51) Int. Cl.
G09B 19/00    (2006.01)
G16H 20/60    (2018.01)

(52) U.S. Cl.
CPC ....... *G09B 19/003* (2013.01); *G09B 19/0092* (2013.01); *G16H 20/60* (2018.01)

(58) Field of Classification Search
CPC .. G09B 19/00; G09B 19/003; G09B 19/0092; G16H 20/60
See application file for complete search history.

(56) References Cited

U.S. PATENT DOCUMENTS

| | | |
|---|---|---|
| 2014/0172313 A1 | 6/2014 | Rayner |
| 2014/0329207 A1* | 11/2014 | Coorey ............. G09B 19/0092 434/127 |
| 2017/0270820 A1 | 9/2017 | Ashby |
| 2020/0113512 A1 | 4/2020 | Tanimura |

* cited by examiner

*Primary Examiner* — Timothy A Musselman
(74) *Attorney, Agent, or Firm* — Boris Leschinsky (57) ABSTRACT

Automated guidance is provided to a subject to build desired chewing habits of food to facilitate adherence to person-specific healthy food intake routine. An electronic device may be configured for operating the automated guiding mode or diagnostic mode. In the automated guiding mode, a subject adopts a sequence presented by the electronic device to form his/her desired chewing habits. In the diagnostic mode, the electronic device proactively analyzes a subject's chewing behaviors via a camera or image sensor to provide guidance to a subject to achieve the desired chewing target.

18 Claims, 4 Drawing Sheets

METHOD AND SYSTEM FOR AUTOMATED GUIDANCE TO A SUBJECT TO BUILD HEALTHY CHEWING HABITS TO FACILITATE ADHERENCE TO A HEALTHY FOOD INTAKE ROUTINE

CROSS-REFERENCE DATA

This US Patent Application is a continuation-in part of and claims a priority date benefit from a corresponding International Patent Application No. PCT/TR2022/050424 filed 17 May 2022 entitled "METHOD AND SYSTEM FOR AUTOMATED GUIDANCE TO A SUBJECT TO BUILD HEALTHY CHEWING HABITS TO FACILITATE ADHERENCE TO HEALTHY FOOD INTAKE ROUTINE", which is incorporated herein in its entirety by reference.

FIELD OF THE DISCLOSURE

The present invention disclosure relates to the field of healthcare systems. More specifically, embodiments of the present disclosure relate to methods and systems for providing automated guidance mode and diagnostic mode to a subject to build healthy chewing habits to facilitate adherence to a healthy food intake routine during meals for better health.

BACKGROUND

Health of human beings is often affected due to various factors, including stressful job, poor nutrition, poor health habits, poor eating habits, poor liquid intake habits, poor chewing habits, monotonous routines, etc. Many people are suffering from health problems, weight control problems, stress, and anxiety, due to which they are unable to lead a healthy normal life. Accordingly, there has been an increase in the usage and consumption of health-related services by people. Many health service providers and organizations provide guidance and recommendations by implementing computer-based platforms to help individuals in maintaining good health. Such organizations also provide remote guidance in order to facilitate the users/consumers in taking care of their well-being from any corner of the world.

However, a review of existing platforms shows that such platforms offer generic advice that may not be effectively helpful to cater to the specific requirements of an individual or community at large. The existing solution for providing health-related services and guidance to users does not provide customized solutions for individuals based on their specific requirements. For example, such solutions fail to guide a user to increase healthy eating, longer chewing, and better drinking habits over a period of time. Being very generic in nature, the existing guidance platforms cannot be applied to all the individuals who need to change their food intake habits and follow a healthy routine. For example, the existing solutions may specifically target weight loss and physical habits and may affect it by analyzing body fat percentage and prior weight measurements. Such solutions fail to facilitate the users to incorporate healthy eating and drinking habits properly in their daily routines. Further, the existing solutions also do not cater to the growing obesity and overweight epidemic through education-driven voluntary lifestyle changes for individuals, families, and communities.

As evident from various published articles, including "Yong Zhu, James H Hollis. *Increasing the number of chews before swallowing reduces meal size in normal-weight, overweight, and obese adults*. PubMed, 9 Nov. 2013", obesity is considered to be associated with various health complications, including hypertension, type 2 diabetes, heart disease, stroke, cancer, and death. Numerous studies found that eating speed/rate and frequency are related to obesity and that eating faster is associated with a higher risk of developing metabolic syndrome and obesity. Specifically, low chewing per bite of food is associated with decreased satiation and greater food intake. Also, some research studies suggest that fast eating is a predisposing factor for new-onset diabetes.

Some clinical trials used the number of chews as an intervention measure to control some health parameters like weight and blood sugar. For example, the article by Jarin Paphangkorakit, Kasama Kanpittaya, Nattawipa Pawanja, Waranuch Pitiphat. *Effect of chewing rate on meal intake*. PubMed, 31 Oct. 2018, found that increasing the number of chews before swallowing might be a behavioral strategy to reduce food intake and potentially aid in weight management. In many of these studies, the chewing rate ranged from 40 to 50 times per bite and could reduce caloric intake regardless of weight status, suggesting that slow eating via increased chewing may help to reduce energy intake during meals. Moreover, some studies found that prolonged chewing can decrease unhealthy eating habits like food cravings and emotional and external eating. In children, data suggest that chewing well is an effective way for healthy weight management among preschool children.

Many studies tried to understand why chewing food well led to increased satiety and weight control. The data suggest that a chewing rate between 40 and 50 chews resulted in an increased concentration of certain hormones like ghrelin, glucagon-like peptide 1, and cholecystokinin. These hormones normally decrease the motility of the stomach leading to a perceived fullness sensation and, hence, satiety. These hormones are produced physiologically in the human body. In fact, an increased chewing rate is found to boost these hormone levels, leading to lower food intake.

This is particularly interesting since increasing the levels of the hormone glucagon-like peptide 1, mentioned above, is the mechanism by which some diabetes medication works—for example, dipeptidyl peptidase-4 (DDP-4) inhibitors and glucagon-like peptide 1 agonists. This might explain why an increased chewing rate can control blood glucose levels.

In view of the above, the subject matter, as disclosed herein, aims to provide a novel system and method for providing automated guidance and guidance to a subject to build healthy eating habits via person-specific chewing needs.

SUMMARY

In order to provide a holistic solution to the above-mentioned limitations, it is required to deploy an interactive platform for providing automated guidance to a subject to build slow eating habits via increased chewing.

It is an object of the present subject matter to provide scientifically validated and reliable automated guidance in order to provide age-, gender- and body mass index-appropriate and timely guidance to facilitate education-driven voluntary eating and chewing lifestyle changes for individuals.

According to an embodiment of the present disclosure, there is provided a method for automated guiding a subject to build a desired healthy food intake routine, the method comprising the following steps:

a. providing an electronic device such as a smartphone, smartwatch, computer, laptop, tablet, or a dedicated stand-alone device, configured for operating in an automated guidance sequence and for generating at least one signal prompt to a subject,
b. initiating the electronic device of step (a) and operating the electronic device to provide a confirmation signal to the subject indicating a start of the automated guiding sequence,
c. operating the electronic device to generate a food intake "bite" signal prompt to invite the subject to take a first bite of food to be consumed,
d. operating the electronic device to generate a series of "chew" signal prompt counts comprising a preselected number of individual chew signal prompt counts spaced apart in time at a preselected frequency,
e. repeating steps (c) through (d) for additional food intake bites and chews until the food is consumed or the automated guiding sequence is stopped.

According to an embodiment of the present disclosure, the signal prompts generated by the electronic device are any one or a combination of an audio prompt, a visual prompt, and a vibratory prompt.

According to an embodiment of the present disclosure, step (c) is performed following a first predetermined delay after step (b) is complete.

According to an embodiment of the present disclosure, step (d) is performed following a second predetermined delay after step (c) is complete.

According to an embodiment of the present disclosure, step (e) is performed following a third predetermined delay after step (d) is complete.

According to an embodiment of the present disclosure, a method for automated guiding a subject to build healthy chewing habits is disclosed. The method comprises the following steps:
a. providing an electronic device configured for operating in an automated guiding sequence and for generating at least one signal prompt, the electronic device is further configured to detect each food intake bite and each food chew facial movement of the subject using an image sensor operatively connected thereto or integrated therewith,
b. initiating the electronic device of step (a) and operating the electronic device to provide a confirmation signal to the subject indicating a start of the automated guiding sequence,
c. operating the electronic device to generate a first food intake "bite" signal prompt to invite the subject to take a first bite of food to be consumed,
d. operating the electronic device to detect and count actual food intake bites via using the image sensor to detect facial movements of the subject corresponding to a food intake bite,
e. operating the electronic device to activate a series of "chew" signal prompts comprising a preselected number of individual audio or video chew signal prompts spaced apart in time at a preselected frequency,
f. operating the electronic device to detect and count actual food chews via using the image sensor to detect facial movements of the subject corresponding to food chewing, and
g. repeating steps (c) through (f) for additional food intake bites and chews until the food is consumed or the automated guiding sequence is stopped.

According to an embodiment of the present disclosure, upon detection in step (f) the actual food chews to be lower than a preselected desired target of food chews, activating a prompt signal to encourage the subject to increase the number of food chews for each food intake bite.

According to an embodiment of the present disclosure, the method further comprises a step of positioning the image sensor in front of the subject.

According to an embodiment of the present disclosure, the method further comprises a step of operating the image sensor to determine either one or both the age of the subject and gender of the subject, the method further comprising a step of generating an age-appropriate, body mass index-appropriate, and/or gender-appropriate chew count target.

According to an embodiment of the present disclosure, the method further comprises a step of recording a history of actual food intake bite counts, chew counts, and liquid consumption amount over time and determining a trend thereof in comparison with the desired target thereof.

According to an embodiment of the present disclosure, a method of automated determination of a sequence and a number of food intake bites, a number of chews in between the food intake bites throughout a single session is disclosed. The method comprises the following steps:
(a) providing an electronic device equipped with an image sensor positioned to view a face of the subject,
(b) operating the electronic device to detect and count the sequence, the number, and the duration of each actual food intake bite and chew via observed jaw and other facial movements of the subject as determined using the image sensor, and
(c) generating a report listing the sequence, the number, and the duration of each food intake bites and chews throughout the eating session.

According to an embodiment of the present disclosure, the report generated in step (c) further comprises a comparison against healthy targets for at least a sequence and a number of food intake bites and chews for the subject.

According to an embodiment of the present disclosure, the healthy targets for the sequence and the number of food intake bites, chews, and drinks for the subject are determined individually based on at least the subject's age and/or the subject's gender.

According to an embodiment of the present disclosure, a system for automated guidance for a subject is provided to form desired chewing habits of food intake or to facilitate adherence to person-specific healthy food intake routine. The system may include an electronic device configured for automatic operation in a predefined guiding sequence and for generating at least one signal prompt. The electronic device may be operably connected to a server and at least one database via a communication network. The electronic device may be configured to detect each food intake bite and food chew facial movements of the subject using an image sensor operatively connected thereto or integrated therewith. The electronic device may be further configured to:
a. generate a confirmation signal to confirm initiation of an automated guiding sequence,
b. automatically generate a first food intake "bite" prompt to guide the subject to take a first bite of food to be consumed,
c. automatically detect and count actual food intake bites via observing the facial movements and detecting the presence of food adjacent to the mouth of the subject using the image sensor,
d. automatically generate a series of "chew" prompt counts comprising a preselected number of individual audio or video chew signal prompt counts spaced apart in time at a preselected frequency, e. automatically detect and count actual food chews by using the image sensor to observe jaw and other facial movements of the subject, and f. automatically repeating steps (c) through (e) for detecting further food intake bites and chews until the food is consumed or the automated guiding sequence is stopped.

According to an embodiment of the present disclosure, upon detecting the actual food chews number to be lower than a preselected desired target of food chews, a prompt signal is automatically activated by the electronic device to guide the subject to increase the number of food chews for each food intake bite.

The aforementioned objectives and additional aspects of the embodiments herein will be better understood when read in conjunction with the following description and accompanying drawings. It should be understood, however, that the following descriptions, while indicating preferred embodiments and numerous specific details thereof, are given by way of illustration and not of limitation. This section is intended only to introduce certain objects and aspects of the present invention, and is, therefore, not intended to define key features or scope of the subject matter of the present invention.

BRIEF DESCRIPTION OF THE DRAWINGS

The figures mentioned in this section are intended to disclose exemplary embodiments of the claimed system and method. Further, the components/modules and steps of a process are assigned reference numerals that are used throughout the description to indicate the respective components and steps. Other objects, features, and advantages of the present invention will be apparent from the following description when read with reference to the accompanying drawings:

Like reference numerals refer to like parts throughout the description of several views of the drawings.

DETAILED DESCRIPTION OF THE INVENTION

The present disclosed subject matter is described with specificity to meet statutory requirements. However, the description itself is not intended to limit the scope of this patent. Rather, the inventors have contemplated that the claimed subject matter might also be embodied in other ways, including different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Reference throughout this specification to "one embodiment" or "an embodiment" means that a particular feature, structure, or characteristic described in connection with the embodiment is included in at least one embodiment of the disclosed subject matter. Thus, appearances of the phrases "in one embodiment" or "in an embodiment" in various places throughout this specification are not necessarily referring to the same embodiment.

Furthermore, the described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

The embodiments used herein are for organizational purposes only and are not meant to be used to limit the scope of the description or the claims. As used throughout this application, the word "may", is used in a permissive sense (i.e., meaning having the potential to), rather than the mandatory sense (i.e., meaning must).

As used herein, 'server' is a computer-based device or a system that facilitates in providing data, services, or programs to various client devices, including any electronic devices, over a communication network. The server may include one or more intelligent processing devices or modules, capable of processing digital logics, and also possesses analytical skills for analyzing and processing various data or information, according to the embodiments of the present invention.

As used herein, 'electronic device' is a smart electronic device and/or smart 'user device' capable of communicating with various other electronic devices and applications via one or more communication networks. Examples of said user devices include, but are not limited to, a wireless communication device, a smartphone, a tablet, a desktop, a laptop, etc. The user device comprises an input unit to receive one or more input data; an operating system to enable the user device/electronic device to operate; a processing unit to process various data and information; a memory unit to store initial data, intermediary data, and final data pertaining to a restaurant and customer-related data; and an output unit having a graphical user interface (GUI).

As used herein, 'database' refers to a local or remote storage device; docket systems; database systems; capable to store information related to health guidance, chew target counts, food bite count, awards or rewards assigned to the users, profiles of users, historical data, chew count being calculated for each user, metadata, etc. In an embodiment, the database may be a database server, a cloud-based storage, a remote database, a local database, and a storage unit.

As used herein, 'module' or 'unit' refers to a device, a system, hardware, or a computer application configured to execute specific functions or instructions according to the embodiments of the present invention. The module or unit may include a single device or multiple devices configured to perform specific functions according to the present invention disclosed herein.

As used herein, 'communication network' includes a local area network (LAN), a wide area network (WAN), a metropolitan area network (MAN), a virtual private network (VPN), an enterprise private network (EPN), Internet, and a global area network (GAN).

Terms such as 'connect', 'integrate', 'configure', and other similar terms include a physical connection, a wireless connection, a logical connection, or a combination of such connections, including electrical, optical, RF, infrared, Bluetooth, or other transmission media, and include configuration of software applications to execute computer program instructions, as specific to the presently disclosed embodiments, or as may be obvious to a person skilled in the art.

Terms such as 'send', 'transfer', 'transmit' and 'receive', 'collect', 'obtain', 'access', and other similar terms refer to the transmission of data between various modules and units via wired or wireless connections across a communication network.

In accordance with the exemplary embodiments, the disclosed computer programs or modules can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl, React Native, Flutter, Swift, Objective-C or other sufficient programming languages.

Figure 1:
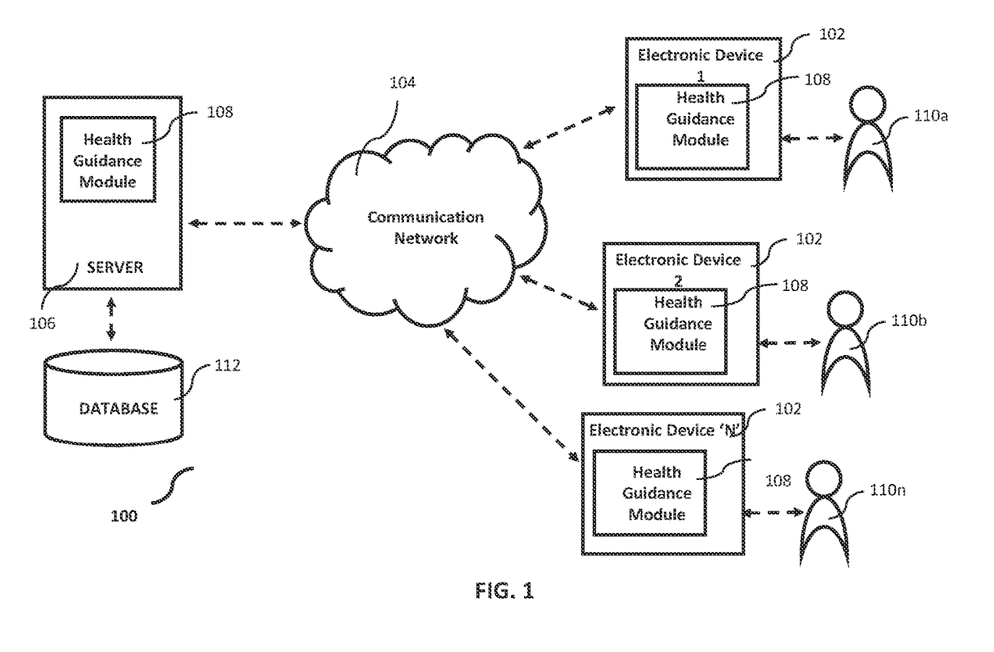
FIG. 1 illustrates a system architecture, according to an exemplary embodiment of the invention disclosure.

FIG. 1 illustrates a system architecture, according to an exemplary embodiment of the invention disclosure. System 100 comprises a server 106, one or more electronic devices 102, and a database 112, operatively connected to each other across a communication network 104. An executable health guidance module 108 may be configured on server 106. Each electronic device 102 may be configured for operating an automated guiding sequence using the health guidance module 108 via server 106. The health guidance module 108 may be configured on the electronic device 102 by following download instructions by respective registered users associated with one or more electronic devices 102. Once the health guidance module 108 has been downloaded on the electronic device, the respective users 110 may be prompted to feed in or input their details in the health guidance module 108. These details may include name, age, gender, personal preferences with respect to food, information pertaining to the health condition of the users 110, such as their stomach health, and/or any other underlying diseases suffered by the respective user, etcetera. Based on the details provided by the users 110, the health guidance module 108 generates their user profile.

The health guidance module 108 comprises a graphical user interface configured for facilitating respective users to interact with the health guidance module 108. The health guidance module 108 interacts with an associated user or subject 110 to automatically guide subject 110 to maintain the desired timing of food and liquid intake, thereby facilitating adherence to healthy food and liquid intake routine to be followed by subject 110. In order to generate specific user profiles, the health guidance module 108 prompts the users to enter details about their expected mealtimes and also about their stomach health, i.e., healthy stomach and unhealthy/gastric stomach. According to the details and the stomach health information, the health guidance module 108 may be configured to send liquid (water) intake reminders or push notifications tailored to the user's health conditions.

The liquid/water intake reminders or push notifications can be modified anytime by the user depending upon the condition of the user's stomach health. For example, a person with a healthy stomach is recommended to drink water or any warm liquid at least thirty minutes prior to each meal and at least two hours after the meal. In addition to this, a person with a healthy stomach is recommended to consume a glass of water every hour as a daily routine. On the other hand, people who have gastric/upset stomachs may drink water at least one hour prior to a meal and three hours after each meal. Further, consuming a glass of water after every hour may provide benefits to individuals with an unhealthy or upset stomach as they may recover faster if they are motivated and are guided in following a correct water intake routine. The health guidance module 108 is configured to guide users 110 to follow the correct food and liquid intake routine by generating timely reminders and push notifications according to the specific needs of the users 110.

The electronic device 102 may further be configured for operating an automated guiding sequence and generating at least one signal prompt for the user or the subject 110. A confirmation signal may be generated by the electronic device 102 to confirm the initiation of the automated guiding sequence to the subject 110 or the user associated with electronic device 102. Thereafter, a food intake "bite" signal prompt may be generated by the electronic device 102, to invite the subject 110 to take the first bite of food to be consumed. The electronic device 102 may further generate a series of "chew" signal prompt counts comprising a preselected number of individual chew signal prompt counts spaced apart at a preselected frequency. Thereafter, a "pause and check hunger sensations" signal prompt at every pre-set bite count for a preselected duration may be generated to allow subject 110 to check his/her hunger sensations. The above steps of generating the food intake "bite" signal prompt, generating the series of "chew" signal prompt counts, and generating the "pause and check hunger sensations" signal prompt of preselected duration may be repeated for any additional food intake bites and chews until the food is consumed or the automated guiding sequence is stopped.

According to an embodiment of the present disclosure step of generating the series of "chew" signal prompt counts is performed following a first predetermined delay after the step of generating the food intake "bite" signal prompt is complete. Further, the step of generating the "pause and check hunger sensations" signal prompt at every pre-set bite count for the preselected duration is performed following a second predetermined delay after the step of generating the series of "chew" signal prompt counts is complete. Furthermore, the step of generating a "pause and check hunger sensations" signal prompt at every pre-set bite count for a preselected duration is performed following a third predetermined delay after the step of generating the series of"chew" signal prompt counts is complete. Apart from building healthy chewing habits, the "drink water" signal prompts prior to food intake and after food intake may be generated according to the stomach health condition of the user 110. For a healthy stomach condition, the user 110 may be given a push notification to drink water at least thirty minutes prior to any meal. On the other hand, if the user is having an upset stomach or gastric stomach, then the push notification or reminder to drink water may be sent at least one hour before any meal to help the user follow the appropriate food and liquid intake routine on a daily basis.

The signal prompts generated by the electronic device 102 are any one or a combination of an audio signal prompt, a visual signal prompt or a video signal prompt, and a vibratory signal prompt. The audio and visual signal prompts may include various audio sounds and videos of a set of predefined types or categories that may be assigned to the different process steps involved in the automated guided sequence. For example, the video signal prompt may include animated videos such as 'Eat Video', 'Chew Video' 'Smile Video', etc., indicating the activation and processing of any of the steps.

The data pertaining to the health guidance may be stored in the database 112 or memories or any storage devices which may be accessed by the electronic device 102 via the server 106. The data pertaining to the health guidance may also be stored in a memory associated with the electronic device 102. The users may be registered with the health guidance module 108 by creating respective user profiles using their respective electronic device 102. Further, the health guidance module 108 may be configured for signal prompting the user to select the number of individual chew signal prompt counts. A chew signal prompt count is a number that may be displayed to the user via the graphical user interface. Users may select any of the displayed chew counts as per their choice and chew their food according to the selected chew count number. According to an embodiment of the present invention, one or more awards, such as a badge or a sticker, may be awarded or assigned to the user for positive reinforcement learning based on a count and a type of task the user has completed successfully.

The electronic device 102 may be authorized by server 106 to execute the health guidance module 108. As mentioned earlier, the server 106 may be connected in communication with the database 112 and the electronic device 102 in the communication network 104. The database 112 may be accessed by the health guidance module 108 to send and receive a plurality of data pertaining to health guidance that is being provided to various users. The server 106 comprises at least one processing unit configured to provide to the electronic device 102, the health guidance module 108 for download and execution. The health guidance module 108 on the electronic device 102 is configured to generate a chew target count for the users according to their requirements for weight control or weight gain. Based on the individual requirement, the chew count target may be set and followed by the users. The electronic device 102 may be configured for operating the automated guiding mode or diagnostic mode via the health guidance module 108. In the diagnostic mode, the electronic device 102 proactively analyzes a subject's chewing behaviors via a camera device or image sensor to provide guidance to a subject to achieve the desired chewing target. Furthermore, the diagnostic mode generates a report about a subject's bite count and chew count information. In the automated guiding mode, a subject adopts a sequence presented by the electronic device 102 to form his/her desired chewing habits.

Figure 2:
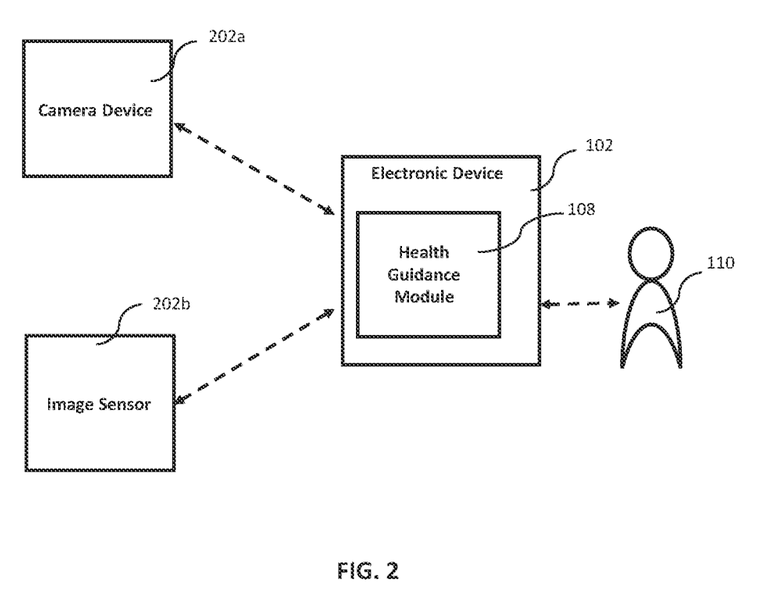
FIG. 2 illustrates a health guidance module, in its diagnostic mode, associated with an image sensor for detecting each food intake bite and food chew facial movement of a subject, according to an exemplary embodiment of the present invention disclosure.

FIG. 2 illustrates a health guidance module 108, in its diagnostic mode, wherein the electronic device 102 is associated with an image sensor 202b for detecting each food intake bite and food chew facial movement of a subject 110, according to an exemplary embodiment of the present invention disclosure. The health guidance module 108 provides automated guidance to the subject 110 to build healthy chewing habits to facilitate adherence to a healthy food intake routine. The electronic device 102 may be configured for operating the automated guiding sequence and generating at least one signal prompt and may be associated with an image sensor 202b or a camera device 202a as shown. The electronic device 102 is thus capable of detecting each food intake bite and food chew facial movement of the subject 110 via the associated image sensor 202b or the camera device 202a. The image sensor 202b or the camera device 202a may be operatively connected to the electronic device 102. In one embodiment of the present subject matter, the electronic device 102 may include an integrated or built-in image sensor 202b or a camera unit 202a to detect the face of the user or the subject 110 while operating the health guidance module 108. The image sensor 202b or the camera unit 202a may be positioned in front of the subject 110 such that the face of the subject 110 is detected and the chewing movement of the jaw made by the subject is counted by the health guidance module 108.

The electronic device 102 is configured to send a confirmation signal to confirm the initiation of automated guidance to the subject 110. Thereafter, a first food intake "bite" signal prompt is generated to invite the subject 110 to take the first bite of food to be consumed. Further, the electronic device 102, via the image sensor 202b or the camera device 202a, detects the facial movements of the subject 110 and counts the number of actual food intake bites. This is accomplished by detecting the jaw movement at the time of chewing a bite. The details of using the image sensor for detecting jaw movements as needed for counting the chews may be found in this publication: S. Gurbuz, K. Kinoshita, M. Riley and S. Yano, "Biologically valid jaw movements for talking humanoid robots," 4th IEEE/RAS International Conference on Humanoid Robots, 2004, Santa Monica, CA, USA, 2004, pp. 781-793, doi: 10.1109/ICHR.2004.1442685.

In addition to detecting actual jaw movement to count the chews, AI-enhanced image processing may be used to observe a movement of the subject 110 in bringing a food utensil with a food bite to the mouth, such as a fork or a spoon. The method of the invention may also be adapted to detect the bringing of food close to the mouth without a food utensil used, such as in case of using one's hands during eating. In further embodiments, false positives may be recognized by not counting a similar action of bringing a napkin close to the mouth to dry or clean the mouth, which may not be accompanied by a definite food bite intake or a food chew to follow.

The actual food intake by the subject 110 is thus detected and counted in real-time while the subject 110 is consuming and chewing the food. In embodiments, some of the food chew counts may be missed, for example, if the subject 110 obstructs the view of the image source by a large food object (such as a large sandwich). The method of the invention may include a step of prompting the subject to remove the object from the view of the image sensor, such as after a predetermined delay. In other embodiments, the chew count between several successive food intake bites may be averaged for improved accuracy. in General, even though some food chews may be missed or misinterpreted, as long as the chew counts and bite counts are recorded with reasonable accuracy, the method would still accomplish the desired goal. Such reasonable accuracy may be at least 95%, at least 90%, at least 85%, or at least 80%.

The electronic device 102 is further configured to activate a series of "chew" signal prompt counts comprising a preselected number of individual audio or video chew signal prompt counts spaced apart at a preselected frequency. In one embodiment of the present subject matter, the preselected frequency includes different ranges for facilitating weight control. A subject 110 may require gaining or losing weight as per the need. Accordingly, the subject 110 may select one of the two 'chew targets' provided for weight control or weight gain. The chew target count for weight control may be provided in a higher range, whereas the chew target count for weight gain may be provided in a lower range.

As mentioned above, the image sensor 202b or the camera device or unit 202a is used for detecting and counting the actual food chew facial movements of the subject 110. This is to ensure whether or not the subject 110 has chewed the food properly. A reward point or score may be assigned upon achieving the target count for every bite of food consumed for positive reinforcement learning for the subject 110. Further, after every pre-set bite count value such as '20', the electronic device 102 may activate a "pause and check hunger sensations" signal prompt at every pre-set bite count for a preselected duration to allow the subject 110 to pause eating to check his/her hunger sensations. The steps of generating the first food intake "bite" signal prompt, detecting and counting the actual food intake bites, generating the series of "chew" signal prompt counts, detecting and counting actual food chew facial movements of the subject 110, and generating a "pause and check hunger sensations" signal prompt at every pre-set bite count for the preselected duration may be repeated for additional food intake bites and chews until the food is consumed or the automated guiding sequence is stopped.

The electronic device 102, upon detecting that the actual food chew facial movements of the subject 110 is lower than a preselected desired target of food chews, then it may generate a signal prompt signal to encourage the subject 110 to increase the number of food chews for each food intake bite. In this way, the target is motivated to chew the food correctly for the required number of chew counts as selected by the user or the subject 110. By accepting the guidance, the subject 110 is made to learn the proper chewing and drinking habits over a period of time and is thus facilitated to maintain health-conscious eating and liquid intake habits and lifestyle.

The health guidance module 108 may further be configured to operate the image sensor 202b to determine either one or both the age of the subject 110 and the gender of the subject 110. Upon detecting the age and gender of the subject 110, the health guidance module 108 generates an age-appropriate and/or gender-appropriate chew count target in accordance with the body mass index for the subject 110. The health guidance module 108 may further be configured to record a history of actual food intake bites, chews, and drinks over time and determine a trend thereof in comparison with the desired target thereof. This helps the subject 110 to analyze the trend over a period of time, and accordingly, the subject 110 is signal prompted to improve their food and liquid intake habits.

According to an embodiment of the present disclosure, the health guidance module 108 is configured to provide an automated determination of a sequence and the number of food intake bites, number of chews in between the food intake bites throughout a single session of consuming food by a subject 110. The first step is initiated by configuring the electronic device 102 that is equipped with an image sensor 202b positioned to view the face of the subject 110. The electronic device 102 is operated to detect and count the sequence, the number, and the duration of each actual food intake bites and chews via observed facial movements of the subject 110 as determined using the image sensor 202b during the single session of consuming the food by the subject 110. Thereafter, a report listing the sequence, the number, and the duration of each food intake bites and chews throughout the single eating session by the subject 110, is generated. The report so generated, further comprises a comparison against healthy targets for at least a sequence and a number of food intake bites and chews for the subject 110. The healthy targets for the number of food intake bites, chews, and daily amount of water for the subject 110 may be determined individually based on at least the subject's 110 age, body mass index, and/or the subject's 110 gender.

Figure 3:
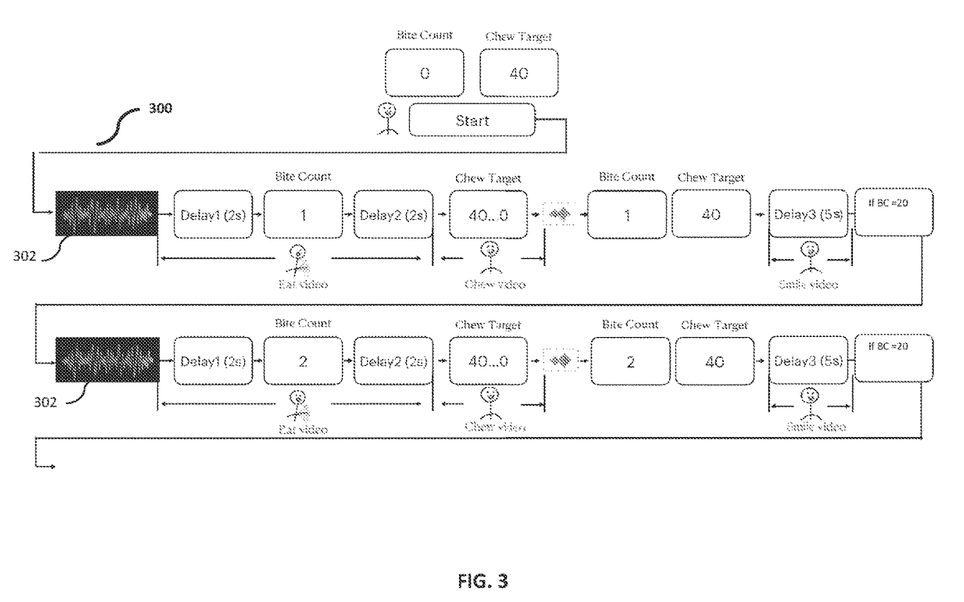
FIG. 3 illustrates the automated guidance sequence for bite signals and chew signals activated for the subject, according to an exemplary embodiment of the present invention disclosure.
Figure 4:
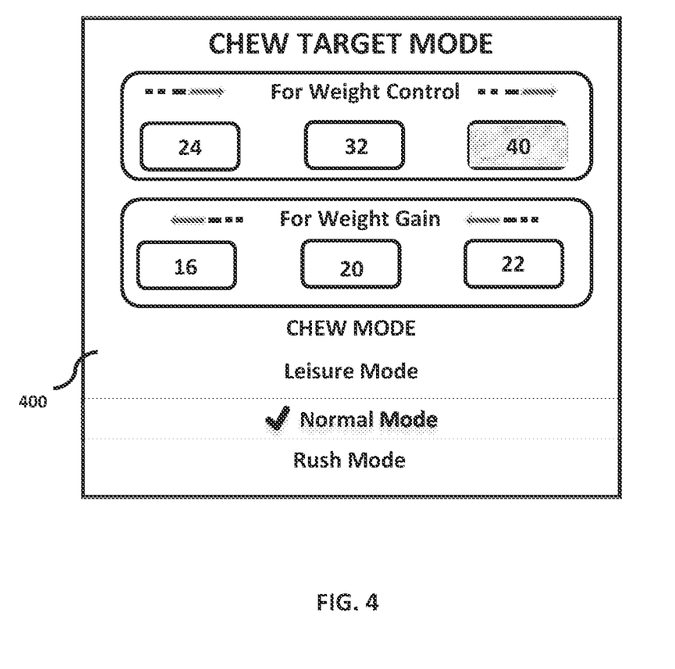
FIG. 4 illustrates the target chew count that can be selected and set by the subject, according to an exemplary embodiment of the present invention disclosure.

FIG. 3 illustrates bite signals and chew signals timings 300 generated for the subject 110, according to an exemplary embodiment of the present invention disclosure. As illustrated in the figure and also explained above, chew target count and chew mode can be predetermined by the health guidance module 108 and can be further preselected by the user 110. The health guidance module 108 facilitates the users to adopt a healthy habit of chewing their food slowly and drinking water many times according to the stomach condition of the user, thereby ensuring superior weight management over time. In an embodiment of the present subject matter, the bite count may be initially set to zero by default when the user or the subject 110 is about to take a first bite of food. At this stage, the chew target count may be preselected by the user. In an event, for example as shown in the figure, that the user 110 selects and sets his/her chew target as '40' then for each bite of food, the user or the subject 110 would be signal prompted to chew each bite 40 times. The preselected chew target count is thereafter decremented starting at "40" (or incremented starting at "1") by one at a time based on the chew mode 400 (as illustrated in FIG. 4), which may be preselected by the subject 110. When the preselected chew target count is complete, the chew target is said to be done by the user for that bite. Then, a "swallow" signal may be provided by playing a corresponding 'sound' 304 and/or video or generating a vibrating effect on the electronic device 102 or a vibrating effect on a wearable device such as a smartwatch worn by the subject 110. The subject 110 may also be prompted by generating signals via videos and sounds 302 to guide the user to take action or conduct a task at the right moment. The videos may be categorized according to different stages of food consumption. For instance, at the beginning of each bite of food, a video for eating ("Eat Video") may be played for the subject 110 on the electronic device 102. Thereafter, for chewing each bite, another video for chewing ("Chew Video") may be played for the subject 110. Once the chew target is complete, an audio or visual signal is generated. Also, an encouragement or positive video ("Smile Video") may be played for the subject 110. Further, a first predetermined delay after the step of generating the food intake "bite" signal prompt is complete, may be generated before guiding the subject 110 to chew the bite for the preselected times, for example 40 chew target count and a two-second (2 s) delay in this example. Furthermore, a second predetermined delay is generated after the step of generating the series of "chew" signal prompt counts is complete. In the example shown in the figure, the second predetermined delay is of two seconds (2 s).

Once the first bite is complete, the subject 110 is signal prompted by another signal to take the second bite. The signal prompt signal may be provided by playing a sound 302 or video or generating a vibrating effect on the electronic device 102 or on a wearable device such as a smartwatch worn by the subject 110. For the second bite also, the subject 110 may be reminded to take the food bite and chew the bite '40' times, as may be preselected, to build conscious chewing habits. The bite count may be incremented by one each time after a bite is consumed by the subject 110. Similarly, for the third bite, the subject 110 may be guided by sending signal prompt signals, playing videos and sounds 302, and guiding to chew the food bite for 'N' number of times as selected by the user.

According to various embodiments of the present subject matter, the health guidance module 108 is further configured to provide 'swallow signals' once the chew count target reaches zero. As mentioned above, the swallow signals may be provided to the subject 110 on respective electronic devices 102 via vibrations, animated videos, sounds 304, etc. Once the chew target drops from 40, as may be preselected, to zero, the time to swallow signal is triggered by the device 102 or smartwatch device worn by the subject 110. As mentioned above, the swallow signal may be an audible signal and/or a vibration.

According to the embodiments of the present subject matter, a fourth predetermined delay may be generated once the bite count reaches a predetermined value. For example, at every 20 bites, the subject 110 may be signal prompted to take a break, such as the "pause and check your hunger sensations" signal prompt. Accordingly, the time delay may be set to ten seconds (10 s), as shown in the figure. Thus, the subject 110 is guided to take breaks at regular intervals. The intervals may be predefined and configurable by the health guidance module 108. Further, if the bite count is set equal to a pre-set number, for example 20, the health guidance module 108 will signal prompt the user 110 to pause and check hunger sensations. The signal prompt is given to the user in the form of a pleasant audible sound, audible voice, video animation, or vibrations. This will give the user 110 an opportunity to check with his/her brain and body. Over time, the small changes in the behavior of the user pertaining to their food and water intake routine, behavior changes proposed in this invention help users to build atomic habits that will lead to a healthy lifestyle such as encouraging being active, chewing each bite of food the required times, drinking water with a person dependent schedule, checking hunger sensations during the meal and making right meal choices.

FIG. 4 illustrates a target chew count 400 that can be selected and set by the subject 110 for achieving weight control or weight gain, according to an exemplary embodiment of the present invention disclosure. Different options for the chew target may be displayed to the user via the user interface to facilitate the user to select the desired chew count. The chew target is a count number that may be predefined on the electronic device 102, and that may be selected by the user according to their needs and requirements to gain weight or lose weight. The chew target mode may be selected for weight gain or weight control by the user. The direction of the arrows in FIG. 4 indicates that the chew target mode may be selected in a lower range for weight gain mode, while it may be selected in a higher range for weight control mode. Further, the user or the subject 110 may be provided with different 'chew modes' categorized into 'Leisure Mode', Normal Mode', and 'Rush Mode'. The chew count may be accordingly selected the subject 110 may select one of the categories for 'chew target modes' provided for weight control or weight gain. The chew target count for weight control may be provided in a higher range, whereas the chew target count for weight gain may be provided in a lower range. For example, in order to achieve weight control, the preferred chew target options provided to the users may include 24, 32, and 40 for chew target, and the chew speed mode may include 'Rush Mode', 'NormalMode', and 'Leisure Mode', and the respective user may select any of the chew target counts and chew speeds depending upon their requirements and other parameters. Similarly, for weight gain, the user may select any of 16, 20, and 22 as their chew target count, and 'Rush Mode', 'Normal Mode', or 'Leisure Mode', as their chew speed mode.

Thus, the embodiments disclosed herein, provide automated guidance to a subject to maintain desired chewing habits of food intake or to facilitate adherence to a person-specific healthy food intake routine. As discussed above, the electronic device 102 may be configured for operating the automated guiding mode or diagnostic mode. In the diagnostic mode, the electronic device 102 proactively analyzes a subject's chewing behaviors via a camera device or image sensor to provide guidance to a subject to achieve the desired chewing target. Furthermore, the diagnostic mode generates reports about a subject's bite counts and chew counts. In the automated guiding mode, a subject adopts a sequence presented by the electronic device 102 to form his/her desired chewing target. In this mode, the food intake "bite" signal prompt may be generated by the electronic device 102 to invite the subject to take the first bite of food to be consumed. Similarly, "swallow" signals may be generated after each target chew count is reached. This may be followed by generating a series of "chew" signal prompt counts comprising a preselected number of individual chew signal prompt counts spaced apart at a preselected frequency. Thereafter, a "pause and check hunger sensations" signal prompt at every pre-set bite count for a preselected duration may be generated to allow the subject to pause eating to check his/her hunger sensations. Apart from adopting healthy chewing habits, drink water push notifications may be generated according to the stomach health condition of the user 110, as explained in the above paragraphs. For additional food intake bites and chews, the above-mentioned steps may be repeated until the food is consumed or the automated guiding sequence is stopped.

According to an embodiment of the present disclosure, a system is provided for automatically guiding a subject to form desired chewing habits of food intake to facilitate adherence to a person-specific healthy food intake routine. The system comprises the electronic device 102 that is configured for operating the automated guiding sequence and generating at least one signal prompt. The same is explained earlier with the help of FIG. 1.

The electronic device 102 is operatively connected to the server 106 and at least one database 112 across a communication network 104. The electronic device 104 is further configured to detect each food intake bite and food chew facial movement of the subject using an image sensor 202b operatively connected thereto or integrated therewith to activate a confirmation signal to confirm initiation of automated guiding. Further, a first food intake "bite" signal prompt may be generated to invite the subject to take a first bite of food to be consumed, detect and count the actual food intake bites via facial movements of the subject, thereby detecting the actual food intake, activate a series of "chew" signal prompt counts comprising a preselected number of individual audio or video chew signal prompt counts spaced apart at a preselected frequency, detect and count actual food chew facial movements of the subject.

Further, in an event, the actual food chews number may be detected and counted to be lower than a preselected desired target of food chews during the diagnostic mode. Thereafter, a signal prompt signal may be generated by the electronic device 102 to encourage the subject to increase the number of food chews for each food intake bite.

It will be understood by those skilled in the art that the figures are only a representation of the structural components and process steps that are deployed to provide an environment for the solution of the present invention disclosure discussed above and do not constitute any limitation. The specific components and method steps may include various other combinations and arrangements than those shown in the figures.

The term exemplary is used herein to mean serving as an example. Any embodiment or implementation described as exemplary is not necessarily to be construed as preferred or advantageous over other embodiments or implementations. Further, the use of terms such as including, comprising, having, containing, and variations thereof, is meant to encompass the items/components/process listed thereafter and equivalents thereof, as well as additional items/components/process.

Although the subject matter is described in language specific to structural features and/or acts, it is to be understood that the subject matter defined in the claims is not necessarily limited to the specific features or processes as described above. In fact, the specific features and acts described above are disclosed as mere examples of implementing the claims and other equivalent features and processes which are intended to be within the scope of the claims.

What claimed is:

1. A method for providing automated guidance to a subject to form desired chewing habits of food intake or to facilitate adherence to a person-specific healthy food intake routine, the method comprising the following steps:
   a. providing an electronic device configured for operating in an automated guidance sequence and for generating at least one signal prompt to a subject,
   b. initiating the electronic device of step (a) and operating the electronic device to provide a confirmation signal to the subject indicating a start of the automated guiding sequence,
   c. operating the electronic device to generate a food intake "bite" signal prompt to invite the subject to take a first bite of food to be consumed,
   d. operating the electronic device to generate a series of "chew" signal prompt counts comprising a preselected number of individual chew signal prompt counts spaced apart in time at a preselected frequency,
   e. repeating steps (c) through (d) for additional food intake bites and chews until the food is consumed or the automated guiding sequence is stopped.

2. The method as in claim 1, wherein the signal prompts generated by the electronic device includes a video signal prompt.

3. The method as in claim 1, wherein step (c) is performed following a first predetermined delay after step (b) is complete.

4. The method as in claim 1, wherein step (d) is performed following a second predetermined delay after step (c) is complete.

5. The method as in claim 1, wherein step (e) is performed following a third predetermined delay after step (d) is complete.

6. A method for providing automated guidance to a subject to form desired chewing habits of food intake or to facilitate adherence to a person-specific healthy food intake routine, the method comprising the following steps:
   a. providing an electronic device configured for operating in an automated guiding sequence and for generating at least one signal prompt, the electronic device is further configured to detect each food intake bite and each food chew facial movement of the subject using an image sensor operatively connected thereto or integrated therewith,
   b. initiating the electronic device of step (a) and operating the electronic device to provide a confirmation signal to the subject indicating a start of the automated guiding sequence,
   c. operating the electronic device to generate a first food intake "bite" signal prompt to invite the subject to take a first bite of food to be consumed,
   d. operating the electronic device to detect and count actual food intake bites via using the image sensor to detect facial movements of the subject corresponding to a food intake bite,
   e. operating the electronic device to activate a series of "chew" signal prompts comprising a preselected number of individual audio or video chew signal prompts spaced apart in time at a preselected frequency,
   f. operating the electronic device to detect and count actual food chews via using the image sensor to detect facial movements of the subject corresponding to food chewing, and
   g. repeating steps (c) through (f) for additional food intake bites and chews until the food is consumed or the automated guiding sequence is stopped.

7. The method as in claim 6, wherein upon detection in step (f) the actual food chews between food bites to be lower than a preselected desired target of food chews, generating a signal prompt to guide the subject to increase the number of food chews after each food intake bite.

8. The method as in claim 6, further comprising a step of positioning the image sensor in front of the subject.

9. The method as in claim 6, further comprising a step of operating the image sensor and the electronic device to automatically determine either one or both an age of the subject and a gender of the subject, the method further comprising a step of operating the electronic device to generate an age-appropriate, body mass index-appropriate, and/or gender-appropriate chew count target.

10. The method as in claim 6, further comprising a step of operating the electronic device to record a history of actual food intake bites and chews over time and determine a trend thereof in comparison with the desired target thereof.

11. A method of automated determination of a number and timing of food intake bites and a number of chews between consecutive food intake bites throughout an eating session of a subject, the method comprising the following steps:
   a. providing an electronic device equipped with an image sensor positioned to view a face of the subject,
   b. operating the electronic device to detect and count the sequence, the number, and the duration of each actual food intake bite and chew via observed jaw and other facial movements of the subject as determined using the image sensor, and
   c. generating a report listing the sequence, the number, and the duration of each food intake bites and chews throughout the eating session.

12. The method as in claim 11, wherein the report generated in step (c) further comprises a comparison against healthy targets for at least a sequence and a number of food intake bites and chews for the subject.

13. The method as in claim 12, wherein the healthy targets for the sequence and the number of food intake bites and chews for the subject are determined individually based on at least the of subject's age, body mass index, and/or the subject's gender.

14. A system for automated guidance for a subject to form desired chewing habits of food intake or to facilitate adherence to person-specific healthy food intake routine; the system comprising an electronic device configured for automatic operation in a predefined guiding sequence and for generating at least one signal prompt, wherein the electronic device is operably connected to a server and at least one database via a communication network, wherein the electronic device is configured to detect each food intake bite and food chew facial movements of the subject using an image sensor operatively connected thereto or integrated therewith, wherein the electronic device is further configured to:
a. generate a confirmation signal to confirm initiation of an automated guiding sequence,
b. automatically generate a first food intake "bite" signal prompt to guide the subject to take a first bite of food to be consumed,
c. automatically detect and count actual food intake bites via observing facial movements of the subject using the image sensor,
d. automatically generate a series of "chew" signal prompt counts comprising a preselected number of individual audio or video chew signal prompt counts spaced apart in time at a preselected frequency,
e. automatically detect and count actual food chews by using the image sensor to observe jaw and other facial movements of the subject, and
f. automatically repeating steps (c) through (e) for detecting further food intake bites and chews until the food is consumed or the automated guiding sequence is stopped.

15. The system as in claim 14, wherein upon detecting the actual food chews number between food bites to be lower than a preselected desired target of food chews, a signal prompt signal is generated by the electronic device to guide the subject to increase the number of food chews after each food intake bite.

16. The system as in claim 14, wherein the image sensor is placed to observe a face of the subject.

17. The system as in claim 14, wherein the electronic device is further configured to operate the image sensor to determine either one or both an age of the subject and a gender of the subject, the electronic device is further configured to automatically generate an age-appropriate, body mass index-appropriate, and/or gender-appropriate chew count target.

18. The system as in claim 14, wherein the electronic device is further configured to record a history of actual food intake bites and chews over time and determine a trend thereof in comparison with the desired target thereof.

* * * * *